US012559780B2

(12) United States Patent
Kang et al.

(10) Patent No.: US 12,559,780 B2
(45) Date of Patent: Feb. 24, 2026

(54) METHOD FOR EFFICIENT CATALYTIC SYNTHESIS OF PAPS BASED ON CONSTRUCTING ATP REGENERATION SYSTEM

(71) Applicant: Jiangnan University, Wuxi (CN)

(72) Inventors: Zhen Kang, Wuxi (CN); Guocheng Du, Wuxi (CN); Ruirui Xu, Wuxi (CN); Yang Wang, Wuxi (CN); Jian Chen, Wuxi (CN)

(73) Assignee: Jiangnan University, Wuxi (CN)

( * ) Notice: Subject to any disclaimer, the term of this patent is extended or adjusted under 35 U.S.C. 154(b) by 410 days.

(21) Appl. No.: 18/192,724

(22) Filed: Mar. 30, 2023

(65) Prior Publication Data

US 2023/0272444 A1    Aug. 31, 2023

Related U.S. Application Data

(63) Continuation of application No. PCT/CN2020/137172, filed on Dec. 17, 2020.

(30) Foreign Application Priority Data

Sep. 30, 2020    (CN) .......................... 202011069179.8

(51) Int. Cl.
*C12N 9/12*        (2006.01)
*C12P 19/40*       (2006.01)

(52) U.S. Cl.
CPC ............ *C12P 19/40* (2013.01); *C12N 9/1241* (2013.01); *C12Y 207/01* (2013.01); *C12Y 207/07004* (2013.01)

(58) Field of Classification Search
CPC ........ C12P 19/40; C12P 19/32; C12N 9/1241; C12Y 207/01025; C12Y 207/01; C12Y 207/04001; C12Y 207/07004
See application file for complete search history.

(56) References Cited

U.S. PATENT DOCUMENTS

| | | | | |
|---|---|---|---|---|
| 5,376,535 | A | * | 12/1994 | Onda ...................... C12P 19/32 |
| | | | | 435/89 |
| 7,057,015 | B1 | * | 6/2006 | Gage ................... C07K 14/721 |
| | | | | 435/325 |
| 12,264,350 | B2 | * | 4/2025 | Fukunaga ...... C12Y 207/07004 |

FOREIGN PATENT DOCUMENTS

| | | | | |
|---|---|---|---|---|
| CN | 101107356 A | | 1/2008 | |
| CN | 105463043 A | * | 4/2016 | ..... C12Y 207/04001 |
| CN | 110982864 A | | 4/2020 | |

OTHER PUBLICATIONS

Thomas S. Leyh, Thomas F. Vogt, and Ya Suo, The DNA Sequence of the Sulfate Activation Locus from *Escherichia coli* K-12, 1992, J.B.C., vol. 267, No. 15, pp. 10405-10410 (Year: 1992).*

(Continued)

*Primary Examiner* — David W Berke-Schlessel
*Assistant Examiner* — Trent R Clarke
(74) *Attorney, Agent, or Firm* — IPRO, PLLC; Na Xu

(57) ABSTRACT

The present disclosure discloses a method for efficient catalytic synthesis of PAPS based on constructing an ATP regeneration system, and belongs to the technical field of bioengineering. Efficient production of PAPS is realized through microbial recombination expression and artificial construction of PAPS bifunctional synthetase. On the basis, an ATP regeneration system coupling with polyphosphate kinase from *Corynebacterium glutamicum* and *Mycobacterium tuberculosis* can be used for recovering two byproducts: pyrophosphoric acid and ADP at the same time, the equivalent conversion of a substrate and a product is realized, the PAPS generated in a catalysis system has high purity, and the sulfonic acid group donation in most sulfonic acid transfer reactions can be realized.

4 Claims, 3 Drawing Sheets

Specification includes a Sequence Listing.

(56)  References Cited

OTHER PUBLICATIONS

Wang, Yanxing "Studies on the mechanism of substrate channeling in sulfate activating complex of phodobacter sphaeroids" Basic Sciences, China Master's Theses Full-text database, No. 05, May 15, 2012. pp. 7-13.

Huang, Yanbo "Construction of sulfate activating complex and pyrophosphatase insertion mutatns of Rhodobacter Sphaeroids" Basic Sciences, China Master's Theses Full-text database, No. 03, Mar. 15, 2014. pp. 11-12.

Li, Hongyan et al. Structural basis analysis of adenosine phosphoacylsulfate channels in sulfate activation complex Proceedings of the Tenth symposium of the Chinese Enzyme Society. Oct. 22, 2011. p. 1.

Xie, Liping et al. Application of cofactor regeneration in biotransformation. Chinese Journal of pharmaceutical biotechnology. V14 No. 6.Dec. 15, 2007. pp. 462-463.

* cited by examiner

METHOD FOR EFFICIENT CATALYTIC SYNTHESIS OF PAPS BASED ON CONSTRUCTING ATP REGENERATION SYSTEM

REFERENCE TO SEQUENCE LISTING

The instant application contains a Sequence Listing in XML format as a file named "YGHY-2022-80.xml", created on Mar. 29, 2023, of 8 kB in size, and which is hereby incorporated by reference in its entirety.

TECHNICAL FIELD

The disclosure relates to a method for efficient catalytic synthesis of PAPS based on constructing an ATP regeneration system, and belongs to the technical field of bioengineering.

BACKGROUND

PAPS (3'-phosphoadenosine-5'-phosphosulfate) is a most important active sulfonic acid donor for a sulfonic acid reaction in vitro, and may be used for sulfonation group donation for chondroitin sulfate, heparin and dermatan sulfate.

At present, PAPS has narrow purchase channel, high price but low purity. The main reason is that the conversion rate of the enzymatic synthesis of PAPS in vitro is low, byproducts are difficult to remove, and the purification of PAPS is difficult.

During enzymatic synthesis of PAPS, two byproducts: pyrophosphoric acid and ADP are mainly produced, so that the theoretical conversion rate of a substrate is only 50%. Recycle of byproducts is an important study contents for efficient production of PAPS. In existing studies, it is mainly started from polyphosphate kinase to convert byproducts for recycle. However, most polyphosphate kinase can only achieve ADP conversion, but cannot achieve pyrophosphoric acid conversion, and the problem that the byproducts cannot be sufficiently utilized still exists.

SUMMARY

Technical Problem

In a process of enzymatic synthesis of PAPS, due to production of byproducts of pyrophosphoric acid and ADP, a great amount of material flow and energy flow are wasted, leading to high PAPS synthesis price and difficulty in obtaining high-purity PAPS. Most of existing reported polyphosphate kinase can only be used for ADP conversion, and cannot realize pyrophosphoric acid conversion. However, during enzymatic preparation of PAPS, the quantity of the byproduct pyrophosphoric acid is also great. If only the ADP can be converted, the rest pyrophosphoric acid cannot be sufficiently used, and the resource waste is caused.

Technical Solution

The inventor selects high-enzyme-activity polyphosphate kinase capable of efficiently utilizing ADP and pyrophosphoric acid from little polyphosphate kinase capable of converting ADP and pyrophosphoric acid at the same time. Based on the screened polyphosphate kinase, the polyphosphate kinase is coupled with a system for enzymatic catalytic synthesis of PAPS, byproducts of pyrophosphoric acid and ADP may be recovered at the same time to synthesize a substrate ATP for continuously participating in the synthesis of PAPS, the synthesis of PAPS without byproducts is realized, high PAPS purity is realized in a catalysis system, and the application is wide. Therefore, the conversion rate of the whole reaction process is improved, the production cost is obviously reduced, and the efficiency is improved.

The disclosure provides a method for synthesizing PAPS. Polyphosphate kinase is added into a reaction for enzymatic conversion synthesis of PAPS. According to the enzymatic conversion synthesis of PAPS, ATP is used as a substrate, and enzymes capable of converting ATP into PAPS are used as catalysts.

In an embodiment of the disclosure, the polyphosphate kinase includes but is not limited to enzymes from *Corynebacterium glutamicum, Mycobacterium tuberculosis, Bacillus aeruginosa* or *Streptomyces*.

In an embodiment of the disclosure, the Gene ID of the polyphosphate kinase from *Mycobacterium tuberculosis* is 888760 (as shown in SEQ ID NO.5).

In an embodiment of the disclosure, the polyphosphate kinase is from *Corynebacterium glutamicum*, and the Gene ID is 1020661 (as shown in SEQ ID NO.4)

In an embodiment of the disclosure, the enzymes capable of converting ATP into PAPS are APS kinase and ATP sulfurylase; or are bifunctional synthetase obtained by linking APS kinase and ATP sulfurylase by a linker.

In an embodiment of the disclosure, the Gen Bank number of the APS kinase is M74586.1 (as shown in SEQ ID NO.2).

In an embodiment of the disclosure, the Gene ID of the ATP sulfurylase is 853466 (as shown in SEQ ID NO.3).

In an embodiment of the disclosure, the sequence of the linker is as shown in SEQ ID NO.1.

In an embodiment of the disclosure, the reaction system also includes sulfate as a sulfate radical donor, and the sulfate includes but is not limited to magnesium sulfate, sodium sulfate and potassium sulfate.

In an embodiment of the disclosure, the sulfate may be preferably magnesium sulfate.

In an embodiment of the disclosure, the substrate ATP and the magnesium sulfate are added into the reaction system, and then, PAPS bifunctional synthetase is added; or APS kinase and ATP sulfurylase are added at the same time, and polyphosphate kinase is added for reaction within 0 to 24 h after a catalysis reaction starts.

In an embodiment of the disclosure, the catalysis system for catalytic synthesis of PAPS includes 50-100 mM of Tris-HCl buffer with a pH value between 7.0 and 8.5, 1-5 mg/mL of PAPS bifunctional synthetase, 1-5 mg/mL of polyphosphate kinase, 5-25 g/L of substrate ATP and 3-15 g/L of magnesium sulfate.

In an embodiment of the disclosure, no ATP detection in the reaction system is regarded as the end of the reaction.

The disclosure provides a method for improving the conversion efficiency of PAPS. Polyphosphate kinase and a phosphoric acid donor are added into a conversion substrate using ATP as a substrate.

In an embodiment of the disclosure, the phosphoric acid donor includes triphosphoric acid, tetra phosphoric acid and/or hexa phosphoric acid.

In an embodiment of the disclosure, the phosphoric acid donor includes sodium tripolyphosphate, sodium tetraphosphate and/or sodium hexaphosphate.

In an embodiment of the disclosure, the polyphosphate kinase includes but is not limited to enzymes from *Corynebacterium glutamicum, Mycobacterium tuberculosis, Bacillus aeruginosa* or *Streptomyces*.

In an embodiment of the disclosure, the Gene ID of the polyphosphate kinase from *Mycobacterium tuberculosis* is 888760 (as shown in SEQ ID NO.5).

In an embodiment of the disclosure, the polyphosphate kinase is from *Corynebacterium glutamicum*, and the Gene ID is 1020661 (as shown in SEQ ID NO.4)

In an embodiment of the disclosure, the reaction system also includes sulfate as a sulfate radical donor, and the sulfate includes but is not limited to magnesium sulfate, sodium sulfate and potassium sulfate.

In an embodiment of the disclosure, the sulfate may be preferably magnesium sulfate.

In an embodiment of the disclosure, the substrate ATP and the magnesium sulfate are added into the reaction system, and then, PAPS bifunctional synthetase is added; or APS kinase and ATP sulfurylase are added at the same time, and polyphosphate kinase is added for reaction within 0 to 24 h after a catalysis reaction starts.

In an embodiment of the disclosure, the catalysis system for catalytic synthesis of PAPS includes 50-100 mM of Tris-HCl buffer with a pH value between 7.0 and 8.5, 1-5 mg/mL of PAPS bifunctional synthetase, 1-5 mg/mL of polyphosphate kinase, 5-25 g/L of substrate ATP and 3-15 g/L of magnesium sulfate.

In an embodiment of the disclosure, no ATP detection in the reaction system is regarded as the end of the reaction.

The disclosure provides a method for improving the recovery efficiency and recovery rate of ADP. Polyphosphate kinase is added into a reaction for synthesizing PAPS, and a phosphoric acid donor is added at the same time. The ADP is a byproduct during PAPS synthesis by using ATP as a substrate.

In an embodiment of the disclosure, the polyphosphate kinase includes but is not limited to enzymes from *Corynebacterium glutamicum, Mycobacterium tuberculosis, Bacillus aeruginosa* or *Streptomyces*.

In an embodiment of the disclosure, the Gene ID of the polyphosphate kinase from *Mycobacterium tuberculosis* is 888760 (as shown in SEQ ID NO.5).

In an embodiment of the disclosure, the polyphosphate kinase is from *Corynebacterium glutamicum*, and the Gene ID is 1020661 (as shown in SEQ ID NO.4)

In an embodiment of the disclosure, the phosphoric acid donor includes but is not limited to pyrophosphoric acid, triphosphoric acid, tetraphosphoric acid and/or hexaphosphoric acid.

In an embodiment of the disclosure, the phosphoric acid donor includes sodium tripolyphosphate, sodium tetraphosphate and/or sodium hexaphosphate.

In an embodiment of the disclosure, the reaction system also includes sulfate as a sulfate radical donor, and the sulfate includes but is not limited to magnesium sulfate, sodium sulfate and potassium sulfate.

In an embodiment of the disclosure, the sulfate may be preferably magnesium sulfate.

In an embodiment of the disclosure, the substrate ATP and the magnesium sulfate are added into the reaction system, and then, PAPS bifunctional synthetase is added; or APS kinase and ATP sulfurylase are added at the same time, and polyphosphate kinase is added for reaction within 0 to 24 h after a catalysis reaction starts.

In an embodiment of the disclosure, the catalysis system for catalytic synthesis of PAPS includes 50-100 mM of Tris-HCl buffer with a pH value between 7.0 and 8.5, 1-5 mg/mL of PAPS bifunctional synthetase, 1-5 mg/mL of polyphosphate kinase, 5-25 g/L of substrate ATP and 3-15 g/L of magnesium sulfate.

In an embodiment of the disclosure, no ATP detection in the reaction system is regarded as the end of the reaction.

The disclosure further protects application of the method for synthesizing PAPS, or the method for improving the conversion efficiency of PAPS, or the method for improving the recovery efficiency and recovery rate of ADP to PAPS preparation.

The disclosure further protects application of the method for synthesizing PAPS, or the method for improving the conversion efficiency of PAPS, or the method for improving the recovery efficiency and recovery rate of ADP to preparation of products using PAPS as raw materials.

The disclosure further protects application of the method for synthesizing PAPS, or the method for improving the conversion efficiency of PAPS, or the method for improving the recovery efficiency and recovery rate of ADP to preparation of products requiring sulfonic acid group donation.

Beneficial Effects

1. The disclosure achieves PAPS preparation by using PAPS bifunctional synthetase. Compared with a traditional two-enzyme synthesis method, the disclosure has the advantages of simple preparation steps of catalysts, high catalysis efficiency and good stability.

2. The disclosure introduces a byproduct recovery system coupling with polyphosphate kinase in a PAPS synthesis reaction, the byproducts of pyrophosphoric acid and ADP can be recovered at the same time, and the equimolar conversion of substrate ATP and PAPS is realized, so that the high-purity PAPS is contained in the synthesized system, and the materials can be used for sulfonic acid group donation in most sulfonic acid transfer reactions without additional purification.

DETAILED DESCRIPTION

Figure 1:
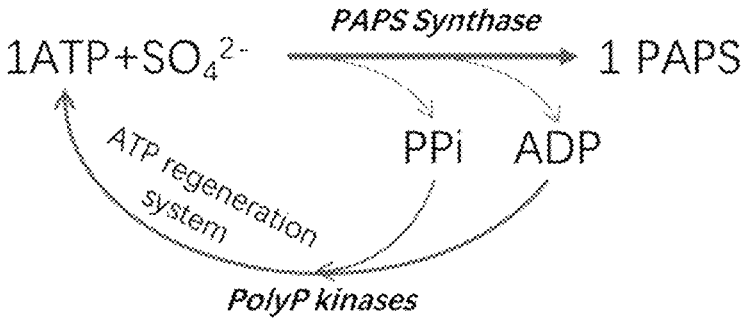
FIG. 1 is a schematic diagram of simultaneous regeneration of two byproducts in a PAPS synthesis system.

Materials:

Bacterial strains and plasmids used in experiments are all preserved in this laboratory.

Various analytical pure reagents are purchased from China National Pharmaceutical Group.

Gene manipulation tools and reagents are purchased from Sangon Biotech (Shanghai) Co., Ltd.

LB culture medium (g/L): 10 of peptone, 5 of yeast powder, and 10 of sodium chloride.

TB culture medium (g/L): 12 of peptone, 24 of yeast powder, 9.4 of $K_2HPO_4$, 2.2 of $KH_2PO_4$, and 5 of glycerol.

ATP detection method: purchased from Beijing Solarbio Science & Technology Co., Ltd. See instructions for use.

PAPS detection method: the following are adopted: an Agilent 1600 HPLC system, a Polyamine II column (4.6× 250 mm, 12 nm), a mobile phase: 50 mM of $KH_2PO_4$ and 0.1% triethylamine solution, a flow velocity: 0.6 mL·min⁻¹, an injection volume: 5 μL, detection time: 35 min, and a detector: UV 254 nm.

PAPS bifunctional synthetase: with ATP sulfurylase and APS kinase activities at the same time.

Definition of enzyme activity of PAPS bifunctional synthetase: the enzyme amount required by synthesis of 1 μM of PAPS per hour under a condition of 37° C.

Definition of enzyme activity of polyphosphate kinase: the enzyme amount required by synthesis of 1 μM of ATP per hour under a condition of 37° C.

Definition of specific enzyme activity: enzyme activity unit number of unit weight (mg) of protein at 37° C.

ATP conversion rate: mole ratio of mole number of product PAPS to substrate ATP.

Example 1: Obtaining of Polyphosphate Kinase (1) The Gene ID of the polyphosphate kinase from *Corynebacterium glutamicum* obtained from NCBI website was 1020661. Through codon optimization, a nucleotide sequence was obtained. A target gene was amplified through a polymerase chain reaction, and was linked to a pRSF-Duet-1 vector to obtain recombinant plasmids. The correctly verified recombinant plasmids were transfected into *E. coli* BL21 (DE3) to obtain a transformant. The transformant was cultured and subjected to sequencing verification, and the correctly verified transformant position was recorded as bacterial strain *E. coli* GluPPK.

(2) Through inquiry, the Gene ID of the polyphosphate kinase from *Mycobacterium tuberculosis* was 888760. Through codon optimization, a nucleotide sequence was obtained. A method similar to step (1) was used to amplify the target gene and link the target gene onto a vector pET32a (+), and the correctly verified recombinant plasmids were transfected into *E. coli* BL21 (DE3) to obtain a transformant. The transformant was cultured and subjected to sequencing verification, and the correctly verified transformant position was recorded as bacterial strain *E. coli* MycPPK.

Induction conditions of bacterial strain *E. coli* GluPPK: 0.3-0.5 mM of IPTG induced expression (30° C., 220 rpm), and expression time of 10-12 h. Kanamycin sulfate with a final concentration of 50 μg/L was added into a culture medium to ensure the plasmid stability.

Induction conditions of bacterial strain *E. coli* MycPPK: 0.1-0.2 mM of IPTG induced expression (20° C., 220 rpm), and expression time of 20-24 h. Ampicillin with a final concentration of 100 μg/L was added into a culture medium.

Figure 2:
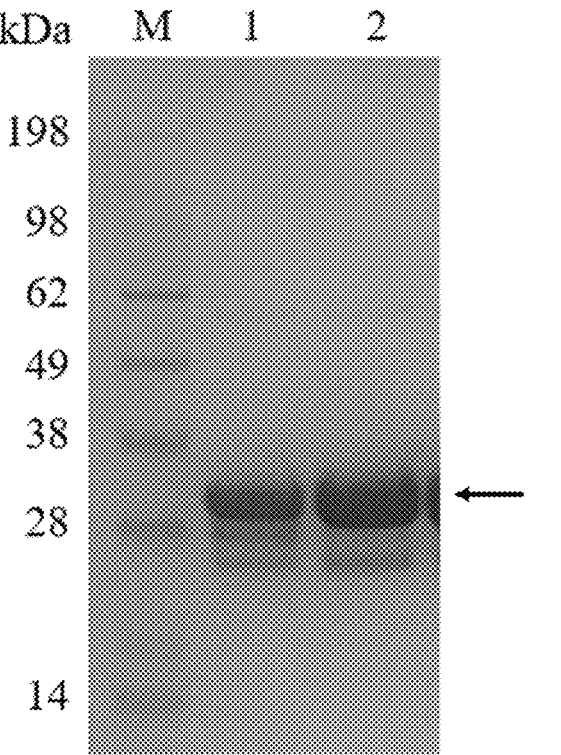
FIG. 2 is an SDS-PAGE diagram of polyphosphate kinase with different sources. Lane 1 is polyphosphate kinase from *Mycobacterium tuberculosis*. Lane 2 is polyphosphate kinase from *Corynebacterium glutamicum*.

Example 2: Purification and Enzyme Activity Comparison of Two Kinds of Polyphosphate Kinase Recombination bacterial strains obtained in Example 1 were cultured for 6-20 h in an LB culture medium. After ultrasonic disruption, collected thalli were subjected to high-speed centrifugation to remove cell debris. The supernatant was filtered by a 0.22 μm water system membrane, and target protein was purified through Ni-NTA affinity chromatography. After column balance of solution A, a crude enzyme was loaded. Then, a chromatographic column was balanced through solution A. Next, the chromatographic column was flushed by B solution of different concentrations, and flushing solution was collected. Purified ingredients (FIG. 2) were verified by SDS-PAGE. The purest ingredients were desalinized through a PD-10 desalinizing column. During desalinization, low-salt buffer (10 mM Tris-HCl, 0.1 M NaCl; pH 6.0) was used, and purified desalinized protein was obtained through collection.

Solution A: 20 mM of Tris-HCl buffer with a pH value of 7.5, and 500 mM of NaCl.

Solution B: 20 mM of Tris-HCl buffer with a pH value of 7.5, 500 mM of NaCl, and 500 mM of imidazole.

Figure 3:
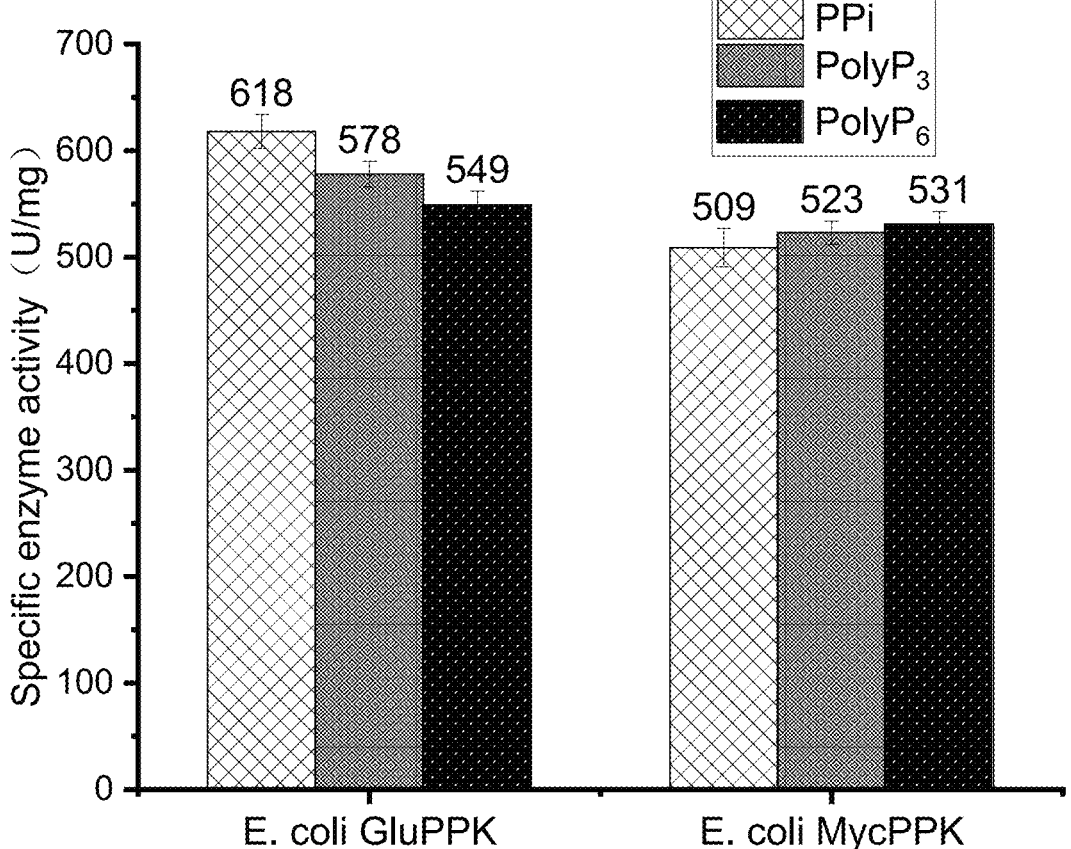
FIG. 3 is enzyme activity determination of polyphosphate kinase from *Corynebacterium glutamicum* and *Mycobacterium tuberculosis*.

After pure enzymes of polyphosphate kinase from different sources were obtained, the same amount of 0.5-1.0 mg/L of pure enzyme and 5 g/L of ADP were added into 50-100 mM of Tris-HCl buffer with a pH value of 7.5 of a catalysis system at the same time. Then, different amount of 2-5 g/L of phosphoric acid donors of sodium pyrophosphate, sodium tripolyphosphate and sodium hexametaphosphate were respectively added. The specific enzyme activity of the polyphosphate kinase was determined by detecting the production of ATP. A reaction temperature was 30-35° C., a reaction time was 12-24 h, and a result was as shown in FIG. 3. The polyphosphate kinase from *Corynebacterium glutamicum* might have higher specific enzyme activity when the sodium pyrophosphate, sodium tripolyphosphate and the sodium hexametaphosphate were used as substrates.

Example 3: Expression, Purification and Enzyme Activity Determination of Bifunctional Synthetase Construction of bifunctional synthetase: ATP sulfurylase (Gene ID: 853466) from *Saccharomyces cerevisiae* and APS kinase (GenBank number: M74586.1) from *Escherichia coli* were fused into one segment (the expression was not influenced by the sequential order of two enzymes) according to a gene manipulation measure. Different fusion linker sequences (linker) were respectively added to linker portions to obtain one segment through fusion, so that the two enzymes maintained a certain spatial position, and the catalysis was more ordered. Specifically, a termination codon of a former gene was removed, the former gene was directly linked to the linker, and was then linked with an initiation codon of another gene. The sequence of the linker was $(GGGGS)_6$. The fusion segment was linked to plasmids pET28a (+), and was transfected into *E. coli* BL21(DE3) to obtain a transformant. The transformant was cultured and subjected to sequencing verification, and the correctly verified transformant position was recorded as bacterial strain *E. coli* CaePAPS. The specific expression manner and enzyme purification methods are the same as those in Examples 1 and 2.

Induction conditions of bacterial strain *E. coli* CaePAPS: 0.1-0.2 mM of IPTG induced expression (25° C., 220 rpm), and expression time of 10-15 h.

Enzyme activity determination: 0.5-1.0 mg/mL of pure enzyme of bifunctional synthetase, 1-5 g/L of a substrate ATP and 0.5-2.5 g/L of magnesium sulfate were added into 50-100 mM of Tris-HCl buffer with a pH value of 7.5 of a catalysis system. The enzyme activity of the PAPS bifunctional synthetase was determined by detecting the production of PAPS in a reaction system. A reaction temperature was 30-35° C., and a reaction time was 24-48 h. The result showed that the enzyme activity is 300±20 U, and the enzyme may be used for subsequent conversion.

Example 4: Efficient Synthesis of PAPS by Coupling ATP Regeneration System

The PAPS was synthesized by using the bifunctional synthetase obtained in Example 3 and the polyphosphate kinase from *Corynebacterium glutamicum* obtained in Example 2.

A 1.5 mL reaction system (50-100 mM Tris-HCl buffer with pH value of 7.5) including 1 mg/mL of PAPS bifunctional synthetase, 1 mg/mL of polyphosphate kinase, 5 g/L of a substrate ATP and 3 g/L of magnesium sulfate was prepared. The adding time of the PAPS bifunctional synthetase was 0 h after the starting of the reaction. The adding time of the polyphosphate kinase was 0-24 h after the starting of the reaction. The reaction ended after 35-50 h of the reaction (no ATP detection in the reaction system was regarded as the end of the reaction). The yield of PAPS was determined after the end of the reaction.

In order to reach higher yield and higher conversion rate, phosphoric acid donors (sodium pyrophosphate, sodium tripolyphosphate and sodium hexametaphosphate) might be additionally added into the catalysis system. The PAPS was prepared and synthesized by using the same method. The only difference was that during reaction, the phosphoric acid donors (sodium pyrophosphate, sodium tripolyphosphate and sodium hexametaphosphate) with a final concentration of 2 g/L were added into the reaction system for reaction. After the end of the reaction, the PAPS was purified, and the yield was determined.

Figure 4:
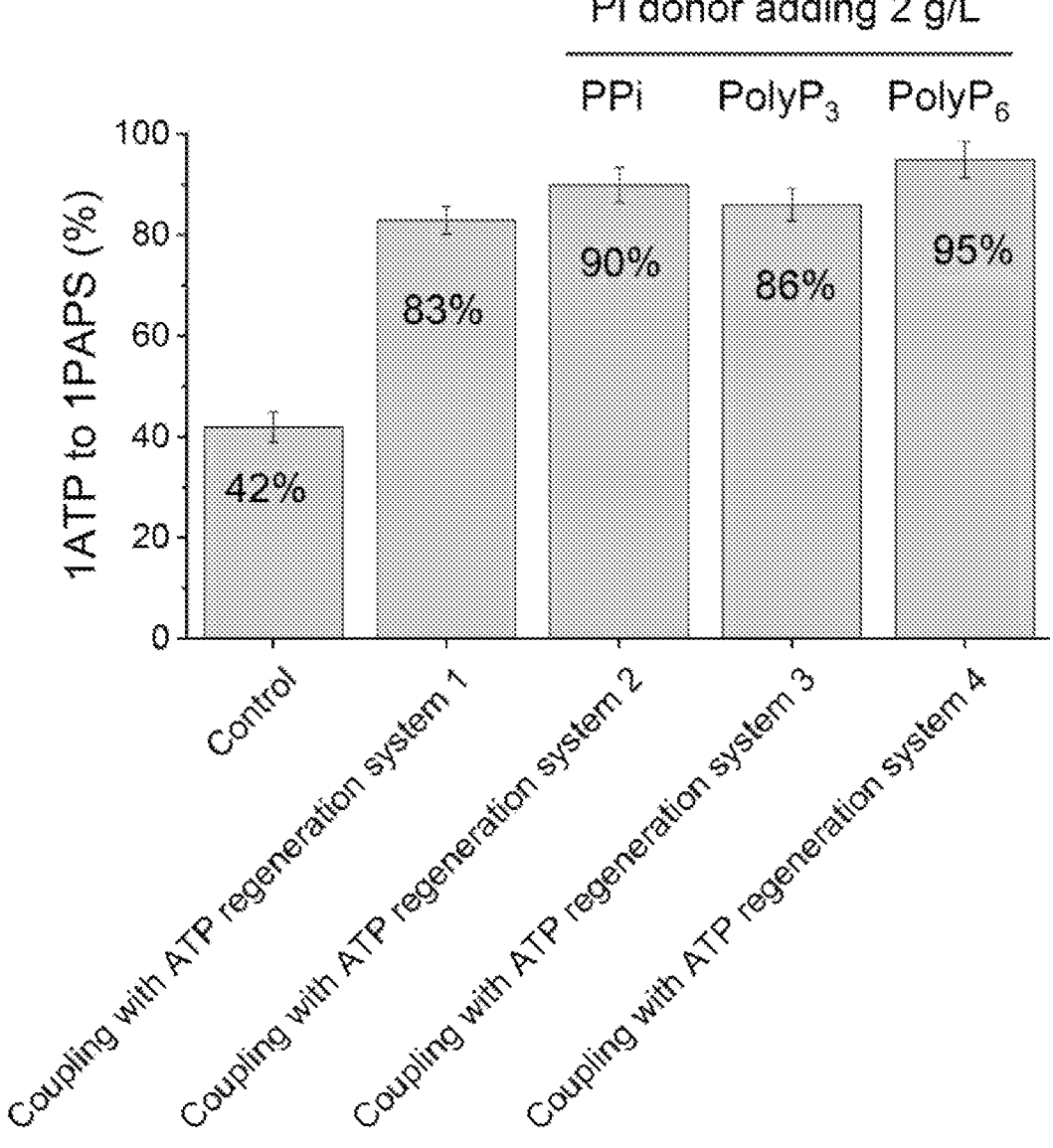
FIG. 4 is the PAPS synthesis conversion rate in different catalysis systems.

The result of the yield was as shown in FIG. 4. After the coupling with the polyphosphate kinase, the conversion efficiency of the substrate ATP is obviously improved, and may be raised from 42% before coupling to 83%-95%.

Although the exemplary Examples of the disclosure have been provided above, they are not intended to limit the disclosure. Those skilled in the art will appreciate that various changes and modifications may be made without departing from the spirit and scope of the disclosure. Therefore, the protection scope of the disclosure shall be defined by the claims.

What is claimed is:

1. A method for synthesizing 3'-phosphoadenosine-5'-phosphosulfate (PAPS), comprising:

incubating adenosine triphosphate (ATP) with adenosine 5'-phosphosulfate kinase (APS kinase), ATP sulfurylase, and polyphosphate kinase, wherein the nucleotide sequence of the APS kinase is as set forth in SEQ ID NO:2, wherein the nucleotide sequence of the ATP sulfurylase is as set forth in SEQ ID NO:3, wherein the APS kinase and the ATP sulfurylase are linked through a sequence with the amino acid sequence set forth in SEQ ID NO: 1, wherein the nucleotide sequence of the polyphosphate kinase is as set forth in SEQ ID NO:4, and wherein a conversion efficiency of the ATP into PAPS is from 83% to 95%.

2. The method according to claim 1, wherein the incubating is performed in the presence of sulfate.

3. The method according to claim 1, further comprising: adding a phosphoric acid donor.

4. The method according to claim 3, wherein the phosphoric acid donor comprises triphosphoric acid, tetraphosphoric acid and/or hexaphosphoric acid.

* * * * *

```
                        SEQUENCE LISTING

Sequence total quantity: 5
SEQ ID NO: 1            moltype = AA  length = 30
FEATURE                Location/Qualifiers
source                 1..30
                       mol_type = protein
                       organism = synthetic construct
SEQUENCE: 1
GGGGSGGGGS GGGGSGGGGS GGGGSGGGGS                                  30

SEQ ID NO: 2            moltype = DNA  length = 606
FEATURE                Location/Qualifiers
source                 1..606
                       mol_type = other DNA
                       organism = synthetic construct
SEQUENCE: 2
atggcgctgc atgacgaaaa cgtcgtctgg catagccatc cggtcactgt gcaacaacgc   60
gagctacacc acggtcatcg tggtgtagtg ctgtggttta ccggcctctc cgggtccggt  120
aaatcaacgg tcgccggggc gctggaggag gcgttacata aactcggcgt cagtacgtat  180
ctgctggatg gcgacaatgt tcgccacgga ttatgcagcg atctcggttt tagcgatgcc  240
gatcgtaaag agaatatccg tcgcgtcggt gaagtggcga atttgatggt tgaagccgga  300
ctggtggtgc tgaccgcatt tatctcgcca caccgcgccg aacgccagat ggttcgcgaa  360
cgcgtaggag aagggcgctt tatcgaagtg tttgtcgatc agccgctggc gatttgcgaa  420
gcccgcgatc ccaaaggctt atataagaaa gcgcgtgccg gtgaactgcg caactttacg  480
ggaatagatt ccgtttacga agcgcctgaa tcggcagaaa ttcatctcaa tggtgaacaa  540
ttagtaacaa atttggtaca gcaattatta gatctgttga gacagaacga tattatcaga  600
tcctga                                                            606

SEQ ID NO: 3            moltype = DNA  length = 1536
FEATURE                Location/Qualifiers
source                 1..1536
                       mol_type = other DNA
                       organism = synthetic construct
SEQUENCE: 3
atgcctgctc ctcacggtgg tattctacaa gacttgattg ctagagatgc gttaaagaag   60
aatgaattgt tatctgaagc gcaatcttcg gacattttag tatggaactt gactcctaga  120
caactatgtg atattgaatt gattctaaat ggtgggtttt ctcctctgac tgggtttttg  180
aacgaaaacg attactcctc tgttgttaca gattcgagat tagcagacgg cacattgtgg  240
accatcccta ttacattaga tgttgatgaa gcatttgcta accaaattaa accagacaca  300
agaattgccc ttttccaaga tgatgaaatt cctattgcta tacttactgt ccaggatgtt  360
tacaagccaa acaaaactat cgaagccgaa aaagtcttca gaggtgaccc agaacatcca  420
gccattagct atttatttaa cgttgccggt gattattacg tcggcggttc tttagaagcg  480
attcaattac ctcaacatta tgactatcca ggtttgcgta agacacctgc ccaactaaga  540
cttgaattcc aatcaagaca atgggaccgt gtcgtagctt tccaaactcg taatccaatg  600
catagagccc acagggagtt gactgtgaga gccgccagag aagctaatgc taaggtgctg  660
atccatccag ttgttggact aaccaaacca ggtgatatga accatcacac tcgtgttcgt  720
gtctaccagg aaattattaa gcgttatcct aatggtattg ctttcttatc cctgttgcca  780
ttagcaatga gaatgagtgg tgatagagaa gccgtatggc atgctattat tagaaagaat  840
tatggtgcct cccacttcat tgttggtaga gaccatgcgg gcccaggtaa gaactccaag  900
ggtgttgatt tctacggtcc atacgatgct caagaattgg tcgaatccta caagcatgaa  960
ctggacattg aagttgttcc attcagaatg gtcacttatt tgccagacga agaccgttat 1020
gctccaattg atcaaattga caccacaaag acgagaacct tgaacatttc aggtacagag 1080
ttgagacgcc gtttaagagt tggtggtgag attcctgaat ggttctcata tcctgaagtg 1140
gttaaaatcc taagagaatc caacccacca agaccaaaac aaggtttttc aattgtttta 1200
ggtaattcat taaccgtttc tcgtgagcaa ttatccattg ctttgttgtc aacattcttg 1260
caattcggtg gtggcaggta ttacaagatc tttgaacaca ataataagac agagttacta 1320
tctttgattc aagatttcat tggttctggt agtggactaa ttattccaaa tcaatgggaa 1380
```

-continued

```
gatgacaagg actctgttgt tggcaagcaa aacgtttact tattagatac ctcaagctca  1440
gccgatattc agctagagtc agcggatgaa cctatttcac atattgtaca aaaagttgtc  1500
ctattcttgg aagacaatgg ctttttgta  ttttaa                            1536

SEQ ID NO: 4              moltype = DNA  length = 900
FEATURE                   Location/Qualifiers
source                    1..900
                          mol_type = other DNA
                          organism = synthetic construct
SEQUENCE: 4
atggctgaaa ccaacgaaaa tgatcttcca gttatcgacc ttgcccaaat cgaaggctat  60
gttgtagatg actcggatga agatgatcca gtacttctgc gtccagatgg aaccccatt   120
gaaacctggc gcgaagactt cccttatgaa gagcgcgtca cccgcgaaga ctatgagaag  180
gtcaagcgct ccctccagat cgagctgctg aagtggcaga actggaccaa ggaaactggc  240
cagcgccaca tcattttgtt cgaagggcgt gacgccgctg gtaagggtgg caccattaag  300
cgcttcaacg aacacctgaa ccctcgtggt gcccgtactg ttgcgttgga gaagccatca  360
ccacgcgaat ccacctcatg gtacttccag cgctatattc agcacttccc agctgctggc  420
gagatcgttt tctttgaccg ctcttggtac aaccgttccg gcgtggagcg cgtcatgggt  480
ttctgcaccg aatcacagca tgcagagttc ctgcgtgagg ttccaatgct ggaaaacatg  540
atcctgggct ctggtatcag cttgaccaag ttctggttct cggtgacccg taaagagcag  600
cgcacccgtt ttgctatccg ccaggttgat cctgtgcgtc agtggaagct ttccccaatg  660
gacttggctt cacttgatcg ctgggatgat tacacccgcg ctaaggaaga gcagttccgt  720
tacaccgaca ctgatgagtc cccgtggatc accatcaagt cgaatgacaa gaagcgtgcg  780
cgtatcaacg cgatgcgtta tgtattgtcc aagtttgatt acaccgacaa ggattacgag  840
ctcgttggtg agcctgaccc taaggttgtg cttcgtgggc gcgaccagat cggtgactag  900

SEQ ID NO: 5             moltype =   length =
SEQUENCE: 5
000
```